United States Patent
Gil et al.

(10) Patent No.: US 12,383,888 B2
(45) Date of Patent: Aug. 12, 2025

(54) VAPOR PHASE METHANOL CARBONYLATION CATALYST

(71) Applicant: ENERKEM INC., Montreal (CA)

(72) Inventors: Jennifer Gil, Montreal (CA); Ariadna Fuente-Hernandez, Montreal (CA); Stéphane C. Marie-Rose, Montreal (CA)

(73) Assignee: ENERKEM INC., West Montreal (CA)

( * ) Notice: Subject to any disclaimer, the term of this patent is extended or adjusted under 35 U.S.C. 154(b) by 215 days.

(21) Appl. No.: 17/614,038

(22) PCT Filed: May 21, 2020

(86) PCT No.: PCT/CA2020/050680
§ 371 (c)(1),
(2) Date: Nov. 24, 2021

(87) PCT Pub. No.: WO2020/237350
PCT Pub. Date: Dec. 3, 2020

(65) Prior Publication Data
US 2022/0250039 A1   Aug. 11, 2022

Related U.S. Application Data

(60) Provisional application No. 62/853,344, filed on May 28, 2019.

(51) Int. Cl.
*B01J 23/63* (2006.01)
*B01J 21/12* (2006.01)
(Continued)

(52) U.S. Cl.
CPC .............. *B01J 23/63* (2013.01); *B01J 21/12* (2013.01); *B01J 21/18* (2013.01); *C07C 51/12* (2013.01); *C07C 67/36* (2013.01)

(58) Field of Classification Search
CPC ... B01J 21/12; B01J 21/18; B01J 23/63; B01J 37/0201; B01J 37/0207; B01J 37/0213;
(Continued)

(56) References Cited

U.S. PATENT DOCUMENTS 3,717,670 A    2/1973  Schultz
4,381,993 A *  5/1983  Nevitt ................... C10G 45/26
                                                        208/260
(Continued)

FOREIGN PATENT DOCUMENTS

CN    1422241        6/2003
CN    103140156      6/2013
(Continued)

OTHER PUBLICATIONS

Kondoh, H. et al., 2018, Physical Chemistry Chemical Physics, 20, 28419-28424 [https://doi.org/10.1039/C8CP05998E]. (Year: 2018).*
(Continued)

*Primary Examiner* — Brian A McCaig
(74) *Attorney, Agent, or Firm* — Norton Rose Fulbirght Canada

(57) ABSTRACT

The present disclosure provides a catalyst for use in a process for methyl acetate and acetic acid production from renewable methanol and synthesis gas. The catalyst comprises at least a metal as an active site for the vapor phase carbonylation reaction, including those from the group VIII and lanthanides series of the periodic table and could be alone or mixed. The support comprises an activated carbon with a high surface area.

20 Claims, 1 Drawing Sheet

(51) Int. Cl.
*B01J 21/18* (2006.01)
*C07C 51/12* (2006.01)
*C07C 67/36* (2006.01)

(58) Field of Classification Search
CPC .......... B01J 37/06; C07C 51/12; C07C 53/08; C07C 67/36; C07C 69/14
See application file for complete search history.

(56) References Cited

U.S. PATENT DOCUMENTS

| | | | |
|---|---|---|---|
| 5,516,967 A | 5/1996 | Pandey et al. | |
| 6,452,043 B1 | 9/2002 | Zoeller et al. | |
| 8,436,215 B2 | 5/2013 | Chornet et al. | |
| 2005/0158235 A1* | 7/2005 | Ramani | C01B 17/046 422/600 |
| 2013/0015103 A1* | 1/2013 | Lapinski | B01J 27/13 208/138 |
| 2013/0165698 A1* | 6/2013 | Powell | C07C 29/60 585/319 |
| 2017/0267523 A1* | 9/2017 | Nakamura | C01B 3/40 |

FOREIGN PATENT DOCUMENTS

| | | | | |
|---|---|---|---|---|
| CN | 105585487 | | 5/2016 | |
| CN | 105585494 | | 5/2016 | |
| CN | 1060140156 | | 11/2016 | |
| CN | 109939746 | | 6/2019 | |
| EP | 1268392 | | 1/2003 | |
| JP | 1994239807 | | 10/1994 | |
| JP | 2003517914 | | 6/2003 | |
| WO | 200048978 A1 | | 8/2000 | |
| WO | WO-0048978 A1 | * | 8/2000 | ............. C07C 51/12 |
| WO | WO-02058822 A1 | * | 8/2002 | ......... B01D 53/8612 |
| WO | WO-2011159268 A1 | * | 12/2011 | ............. C07C 51/12 |

OTHER PUBLICATIONS

Innes, W.B., 1954, "Catalyst Carriers, Promoters, Accelerators, Poisons, and Inhibitors," in Catalysis, vol. 1 Fundamental Principles, edited by P.H. Emmett, Reinhold, 394 pp. [Office action cites p. 272]. (Year: 1954).*

* cited by examiner

VAPOR PHASE METHANOL CARBONYLATION CATALYST

CROSS-REFERENCE TO RELATED APPLICATION

The present application is a U.S. National Phase of International Application no. PCT/CA2020/050680, filed May 21, 2020, and claiming priority from U.S. Provisional Application No. 62/853,344 filed May 28, 2019, the content of which are hereby incorporated by reference in its entirety.

TECHNICAL FIELD

The present relates to a catalyst for vapor phase carbonylation of renewable methanol and synthesis gas to produce methyl acetate and/or acetic acid, and a method of making the catalyst.

BACKGROUND

Methanol carbonylation is a well-known process developed for acetic acid production. The first catalyst used for this reaction was a Co-based catalyst developed by BASF (Hohenschutz et al., 1966, Hydrocarbon Process, 45: 141). However, this process reaction suffered significantly low selectivity and the requirement of high conditions of temperature and pressure.

A rhodium (Rh) based catalyst was introduced by Monsanto for acetic acid production, which became the predominant catalyst and one of the most successful examples of the commercial application of homogeneous catalysis. Over the years, there has been considerable research activity to develop a new Rh based catalyst for homogeneous methanol carbonylation. U.S. Pat. Nos. 5,144,068 and 6,657,078 describe catalysts which use less water than the conventional Monsanto catalyst.

U.S. Pat. No. 3,689,533 discloses a rhodium catalyst made from the decomposition of rhodium nitrate that is supported on pumice, alumina, silica, silica-alumina, bauxite, titanium, zirconia, clays, lime, magnesium silicate, silicon carbide, activated and non-activated carbon, ceramic honeycombs and porous or organic polymers in the presence of a halide promoter (1 to 20 wt %). The rhodium concentration on the support is between 0.1 to 5 wt %. U.S. Pat. No. 3,717,670 describes a similar supported rhodium catalyst in combination with promoters selected from groups I, III, IV, V, VI, VIII, lanthanide and actinide series elements.

It is disclosed in European application no. 0461802 a carbonylation catalyst (rhodium based) supported on a carbon derived from phenolic resin which has been partially cured, ground, shaped carbonized and activated by heating with alkali metal hydroxide and/or heating in an oxidizing atmosphere. U.S. Pat. No. 4,417,077 teaches the use of anion exchange resins bonded to anionic forms of a single transition metal (rhodium, cobalt, ruthenium, osmium, iridium or iron) as catalysts for several carbonylation reactions including the halide-promoted carbonylation of methanol. Although supported ligands and anion exchange resins may be of some use for immobilizing metals in liquid phase carbonylation reactions, in general, the use of supported ligands and anion exchange resins offer no advantage in the vapor phase carbonylation of alcohols compared to the use of the carbon as a support for the active metal component.

Methyl acetate synthesis from methanol gas phase carbonylation is disclosed in U.S. Pat. No. 5,488,143 wherein a rhodium-based catalyst in the presence of halide co-catalyst is used. The rhodium catalyst includes a rhodium compound and a second metallic component selected from the group consisting of an alkali metal, an alkali earth metal, transition metal and a mixture thereof; supported on an inert material.

Despite many efforts and substantial development, there is still a need to be provided with a rhodium catalyst for vapor phase methanol carbonylation process with a low concentration of rhodium, with the aim of improving the active rhodium complex stability as described in Monsanto catalytic cycle over the inert support and the better impregnation of the active phase on the support for the gas phase methanol carbonylation reaction.

Most of all catalysts developed for the methanol carbonylation reaction are mainly for liquid phase processes. The improvement of the liquid catalysts is mainly to prevent catalyst precipitation in the liquid media.

SUMMARY

It is provided a gas phase carbonylation catalyst comprising at least one element from group VIII of the periodic table, a lanthanide or a mixture thereof; and an inert support.

In an embodiment, the element from group VIII and lanthanides are in an oxide form.

In another embodiment, the element from group VIII is iron, ruthenium, osmium, hassium, cobalt, rhodium (Rh), iridium, nickel, palladium or platinum.

In a particular embodiment, the catalyst comprises rhodium (Rh) and lanthanide (La).

In an embodiment, the catalyst comprises a Rh—La dispersion greater than 80%.

In a further embodiment, the element from group VIII is at least one of cobalt, rhodium, iridium, nickel, and a mixture thereof.

In an embodiment, the element is a combination of metals.

In an additional embodiment, the combination of metals is rhodium-cobalt, nickel-rhodium, rhodium-iridium, iridium-cobalt, iridium-nickel, or nickel-cobalt.

In a further embodiment, the combination of metals is rhodium-cobalt or iridium-cobalt.

In a supplemental embodiment, the combination of metals is rhodium-cobalt-iridium.

In an embodiment, the catalyst comprises between 0.01 wt % to 1 wt % of the element compared to the total weight of the catalyst.

In an embodiment, the catalyst described herein comprises at least one transition metal.

In an embodiment, the catalyst described herein comprises at least one promotor from group III of the periodic table.

In an embodiment, the promotor is scandium, yttrium, lanthanum, an actinide or a mixture thereof.

In a further embodiment, the catalyst described herein comprises lanthanide, yttrium or a mixture thereof.

In an embodiment, the catalyst comprises between 0.01 wt % to 1 wt % of the promotor compared to the total weight of the catalyst.

In an embodiment, the catalyst comprises 0.6% Rh-0.4% La or 0.2% Rh-0.2% La.

In a further embodiment, the support is an activated carbon.

In a further embodiment, the support is a zeolite.

In an embodiment, the support is alumina.

In a further embodiment, the support is chemically pretreated increasing the support surface oxygen groups.

In another embodiment, the support is chemically pretreated with an acid treatment.

In a further embodiment, the acid treatment is a treatment with $HNO_3$, and the oxygen groups are lactone, quinone, carboxylic, or phenols.

In an embodiment, the catalyst described herein is for a vapor phase carbonylation of renewable methanol.

It is also provided a process of carbonylation of methanol comprising the step of reacting in a gas phase in a carbonylation reactor the methanol, carbon monoxide in the presence of the catalyst as described herein, producing a mixture of methyl acetate, acetic acid, water, unreacted methanol and dimethyl ether (DME).

In an embodiment, the carbonylation reactor is a fixed bed reactor.

In an embodiment, the gas phase is a vapor phase.

In a further embodiment, the catalyst is activated with carbon monoxyde, a synthesis gas, or a mixture thereof, prior to the reacting step.

In another embodiment, the selectivity of producing methyl acetate is of at least 80%.

In an additional embodiment, the selectivity of producing methyl acetate and acetic acid is of about 88% and 4.3% respectively.

In a further embodiment, the methanol is renewable methanol.

In another embodiment, the renewable methanol is from Municipal Solid Waste (MSW), biomass, or algae.

DETAILED DESCRIPTION

Figure 1A:
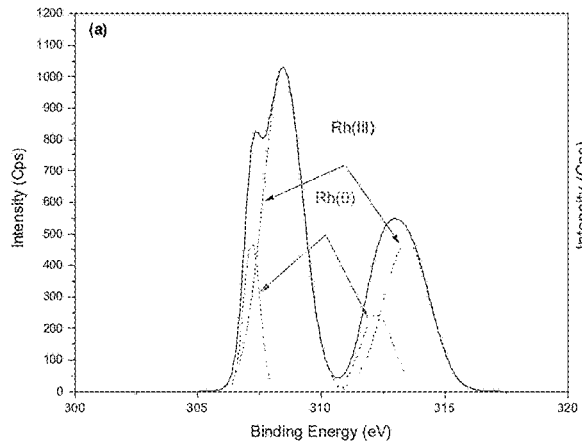
FIG. 1A illustrates a graph showing four XPS peaks observed in the region of 300 to 330 eV indicative of $Rh^{+3}$ and $Rh^0$ oxidation states.

It is provided a catalyst comprising an element from group VIII of the periodic table, a lanthanide series alone and/or mixed and an inert support comprising an activated carbon with a high surface area.

In one aspect described herein, there is provided a gas phase carbonylation catalyst process employing a rhodium-lanthanide complex dispersed on an inert support, able to prevent deactivation of the active phase by sintering and/or leaching for acetic acid and methyl acetate synthesis. In the aforementioned process, a catalyst comprising at least one metal active for the carbonylation reaction chosen from the metal transition group VIII of the periodic table is used, alone or combined with lanthanide series, both in oxide form dispersed on an inert support.

Renewable methanol derives from a feedstock having biogenic carbon such as, for example but not limited to, and as encompassed herein, Municipal Solid Waste (MSW), biomass, or algae. In one embodiment, renewable methanol is defined by methanol having at least 0.01% biogenic carbon, preferably 1% biogenic carbon. Biogenic carbon content in the feedstock or the methanol is measured according to the ASTM D 6866 method.

Sintering and leaching phenomena are the main cause of deactivation of active metal on the catalyst when they are used in gas phase reaction. The catalysts provided herein address these issues with extended time on stream and cycle reduction on activation/operation/regeneration or frequent catalyst reloading to the reactor. Thus, the catalysts provided herein are vapor phase carbonylation catalysts with low Rh concentration, which shown to be resistant to leaching and sintering effect.

Accordingly, the catalysts provided herein are for gas phase carbonylation. Therefore, the catalyst as described herein increases the lifetime of the Rh based catalyst used in gas phase methanol carbonylation process such as, for example, those mentioned in U.S. Pat. No. 8,436,215 or 8,088,832, while using lower concentrations of Rh on the support.

It is also encompassed a process employing a catalyst, as described herein, comprising at least an active metal for the carbonylation chosen from the group formed by the transition metal, group VIII of the periodic table alone or mixed with lanthanide series elements.

In an embodiment, the elements of group VIII of the periodic table include iron, ruthenium, osmium, hassium, cobalt, rhodium (Rh), iridium, nickel, palladium, and platinum. Preferably, group VIII element is at least one element of cobalt, rhodium, iridium, nickel, and a mixture thereof. In the case of the catalyst is only made from elements of group VIII of the periodic table, the following metals combination are preferred: rhodium-cobalt, nickel-rhodium, rhodium-iridium, iridium-cobalt, iridium-nickel, or nickel-cobalt.

In another embodiment, the catalyst comprises a mixture of rhodium-cobalt or iridium-cobalt. It is also encompassed the use of a combination of three metals such as, for example, rhodium-cobalt-iridium.

In the case that the catalyst composition comprises at least one transition metal of the group VIII of the periodic table, the transition metal content on an oxide basis must be between 0.01 wt % and 1 wt % compared to the total weight of the catalyst.

In the case that the catalyst composition comprises at least one transition metal, the catalyst may also include at least one promotor, from group III. Group III in the periodic table comprises scandium, yttrium, the lanthanide and actinide series elements. In an embodiment, the group III element encompassed herein consists of lanthanum (La), yttrium, alone or as a mixture. In an embodiment, the concentration of the promoting element is preferably between 0.01 and 1 wt % compared to the total weight of the catalyst.

As encompassed, the catalysts described herein comprise a support for the active phase dispersion. In a further embodiment, the support encompassed herein is an activated carbon. Preferably, the support is a zeolite material with very low acidity. In an embodiment, the support is alumina (alpha, beta or delta).

In one aspect, the active metal or active alloy (complex) encompassed herein can be coordinated with an organic ligand to form a material having 1 to 3-dimension structure. The resulting material from this coordination may be analogous to a cluster or a coordination polymer.

The support used for the synthesis of the catalyst as described herein is preferably activated carbon, wherein the nature and concentration of the surface functional groups are modified by suitable chemical treatment to increase the surface oxygen groups. The surface oxygen-groups on the activated carbon are carboxylic, carbonyls, phenol, quinone, and lactone. As encompassed herein, the use of a chemical treatment increases the concentration of the oxygen groups to create a strong bonding between the support and the metals. In one embodiment, the metal is Rh alone. In another embodiment, but not limited to, the metal is the "active alloy" Rh—La.

A semi-qualitative indication of the nature of the aforementioned surface oxygen-groups can be obtained by determining the pH of an aqueous suspension of the activated carbons (fresh and treated activated carbons, as well as impregnated after and before carbonylation reaction). Acidic sites may be of the Brønsted type (proton donor) or of the Lewis type (electron acceptor). The three factors to consider to assess the acidity of solids are the concentration, the strength, and the type of acid sites.

Boehm titration is used to quantify functional oxygen-groups on the activated carbons surface and estimate their acidic and basic properties. The method is based on acid/base titration of carbon acidic and basic centers and is generally described by Salame and Bandosz in "Experimental Study of Water Adsorption on Activated Carbon" in LANGMUIR, Volume 15, Issue 2, (1999) pp 587-593.

Acid/Base Titration Method

Boehm acid/base titration of both pretreated and Rh—La supported activated carbons is used to quantify functional groups on the surface and estimate their acidic properties. Activated carbons are placed in clean and dry containers for conducting the experiments and 0.05N solutions in distilled (or demineralized) water each of sodium hydroxide (NaOH), hydrochloric acid (HCl), sodium carbonate ($Na_2CO_3$), and sodium bicarbonate ($NaHNO_3$) are prepared and standardized.

1.5 g of the carbon to be analyzed are placed in each of three containers. Into the first vial, 50 mL of the NaOH 0.05N solution are added. Into the second vial, 50 mL of $Na_2CO_3$ 0.05N solution are added. And into the third vial, 50 mL of $NaHNO_3$ 0.05 N solution are added. The three vials are then individually sealed and stirred for 24 hours at room temperature.

Samples from each of the vials are filtered through 0.2 micron filter paper from Whatman. In turn, 10 mL aliquot from each of the filtered solutions (sodium hydroxide, sodium carbonate, and sodium bicarbonate) are pipetted into separate individual clean bubblers. To ensure complete neutralization of the base, $NaHCO_3$, and NaOH excess bases are neutralized with 20 mL of standardized 0.05N HCl solution, while $Na_2CO_3$ base excess is neutralized with 30 mL of standardized 0.05N HCl solution.

The acidified solutions are then degassed for 1-4 hours, preferably for 2-3 hours by bubbling an inert gas. The size of the bubbles should be between 1 and 5 mm in diameter, preferably between 1-3 mm in diameter, but more preferably between 1-2 mm in diameter. The inert gas flow must be less than 5 mL/min, preferably less than 3 mL/min, but more preferably less than 2 mL/min.

The acidified and degassed $NaHCO_3$, $Na_2CO_3$, and NaOH base solutions are then titrated at 25° C. with a standardized 0.05N NaOH solution while being continuously saturated with an inert gas. The endpoint is determined using a pH meter. The titrant solution is measured using a 25 mL burette with 0.1 mL divisions as it is added.

The number of acidic sites is calculated as follows:

$$[HCl] \; V_{(HCl \; acidif)} = [NaOH] \; V_{NaOH} + \left( \frac{n_{HCl}}{n_B} [B] V_B - n_{CSF} \right) \frac{V_{aliquot}}{V_B}$$

$$n_{CSF} = \frac{n_{HCl}}{n_B} [B] \; V_B - ([HCl]V_{(HCl \; acidif)} - [NaOH]V_{(NaOH \; tit)}) \frac{V_B}{V_{aliquot}}$$

where [B] and $V_B$ are the concentration and the volume of the reaction base mixed with carbon to be analyzed, respectively, providing the number of moles of reaction base available for the surface of carbon for reaction with the surface functionalities. $n_{CSF}$ denotes the moles of carbon surface functionality (CSF) which reacted with the corresponding base during the mixing step. $V_{aliquot}$ is the volume of the aliquot taken from the $V_B$, and [HCl] and $V_{(HCl \; acidif)}$ are the concentration and volume of the acid added to the aliquot taken from the initial sample, respectively. This gives the number of moles of acid added to the aliquot, which are available for reaction with the remaining base.

The results thereby obtained are set forth in Table 1 and they are recorded as meq/100 g (or milliequivalents/100 grams) of activated carbon sample. Meq is an abbreviation for the equivalent weight in milligrams, which is recommended as an international unit.

TABLE 1

Acidity measured by Boehm titration (meq/100 g of carbon)

| | Oxygen Group | | | |
|---|---|---|---|---|
| | C | P | L | Total |
| Fresh Carbon | 0 | 0 | 0 | 0 |
| Pretreated Carbon | 97.97 | 263.51 | 50.92 | 412.40 |
| 0.6% Rh—0.4% La before reaction | 141.86 | 259.25 | 28.34 | 429.45 |
| 0.6% Rh—0.4% La after reaction | 77.83 | 194.11 | 68.06 | 340.00 |

Legend: Carboxylic group (C); Phenolic group (P); Lactone group (L).

An increase of almost 44 meq/100 g of carbon in the carboxylic groups is observed in pretreated supports impregnated with Rh—La, what comes from a creation of a strong bonding between the support and added metals and an increase of their adsorption in those sites. Regarding the single-bonded oxygen functional groups after impregnation process and before carbonylation reaction, phenolic groups do not show a significant difference, while lactone groups decrease near to 22 meq/100 g of carbon.

Interestingly, the determination of oxygen-groups after the carbonylation reaction show that the reaction has a preference to occur at carboxylic and phenolic groups due to the observed decrease of both of almost 65 meq/100 g of carbon, while there is a generation of surface lactone functional groups, taking into account the increase in their value (near to 40 meq/100 g of carbon). However, these variations observed in the surface oxygen-groups of the catalyst after the carbonylation reaction are not substantial, which means that the catalyst has a relatively high stability and is not very sensitive to leach.

In one embodiment, the total acidity (which includes the carboxylic, lactone, and phenolic groups) is determined by Boehm titration with NaOH.

In another embodiment carboxylic and lactone groups are determined by Boehm titration with $Na_2CO_3$.

In a further embodiment the acidity corresponding to carboxylic group is determined by Boehm titration with $NaHCO_3$.

Notice that acidity corresponding to phenolic group on the surface can be easily calculated by the difference between the total acidity measured with NaOH and the acidity measured with $Na_2CO_3$. On the other hand, acidity corresponding to lactone group on the surface can be also calculated by the difference between the acidity measured with $Na_2CO_3$ and $NaHCO_3$ solutions.

Elemental Analysis and Particle Size

As encompassed herein, the catalyst comprises a combination of Rh and La with the support. This combination implies that the La acts as an anchor for the Rh on the activated carbon support, leading to a better binding of the active alloy Rh—La on the support. In an embodiment, the active alloy is at least composed of one Rh atom. The latter is the active center or active site for the gas phase carbonylation reaction.

In a further embodiment, the catalyst for the gas phase methanol carbonylation process described herein is a Rh dispersion on the activated carbon (the support). The low Rh and La particles sizes shown in Table 2 are an indication that the Rh—La alloy particles are well dispersed on the support.

TABLE 2

Rh and La particle size of 0.6% Rh—0.4% La catalyst.

| Before operation | | After operation | |
|---|---|---|---|
| Rh (nm) | La (nm) | Rh (nm) | La (nm) |
| 2.21 | 2.06 | 2.33 | 2.30 |

In one embodiment the catalyst has a Rh—La dispersion greater than 80%, preferably 90% and more.

In another embodiment, the catalyst is resistant to leaching. The leaching effect is tested to determine the chemical stability of Rh—La on the activated carbon support. Once impregnated, the catalysts with different Rh—La contents are dipped separately for two weeks in HCl (37%) solution and then dried at 50° C. during 12 h. The recovered samples are characterized by elemental analysis (see Table 3).

TABLE 3

Elemental analysis of 0.6% Rh—0.4% La catalyst.

| Treatment | | Fresh | HCl (37%) 2 week |
|---|---|---|---|
| On the Catalyst | Rh (mg) | 55 ± 2.1 | 57 ± 0.3 |
| | La (mg) | 42 ± 0.3 | 15 ± 0.4 |
| In the liquid collected after pretreatment | Rh (mg) | — | 3 ± 0.05 |
| | La (mg) | — | 46 ± 4 |

As demonstrated herein, the encompassed catalyst presents a high resistance to leaching under HCl (37%) since only 0.1% Rh—La is leached, keeping similar size distribution than non-pretreated catalyst.

The catalyst encompassed herein is preferably prepared by co-impregnation of a Rh salt i.e. complexed with an organic ligand or in oxide form and La oxide powder or complexed with an organic ligand, dissolved in an acid media to improve the solubility of the salt and the powder.

Before the use of the catalyst described herein for the gas phase methanol carbonylation reaction, the catalyst is activated. According to one embodiment, the catalyst is preferably activated with carbon monoxide prior to the reaction. It is described herein that the pretreatment conditions can influence the formation of carbonylation products, and the most active catalyst is obtained in the presence of CO. To probe the role played by the activation conditions on the catalyst and especially on the oxidation state of Rh, the catalyst is examined by in situ X-ray Photoelectron Spectroscopy (XPS) to ascertain oxidation states after exposure to carefully control activation conditions.

Figure 1B:
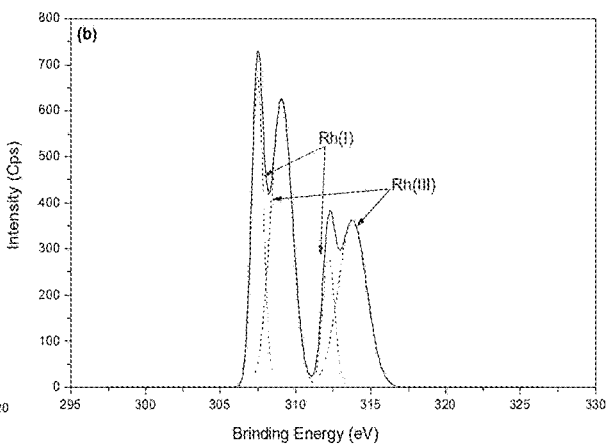
FIG. 1B illustrates a graph showing a spectrum suggesting the presence of $Rh^{+1}$ and $Rh^{+3}$.
Figure 1C:
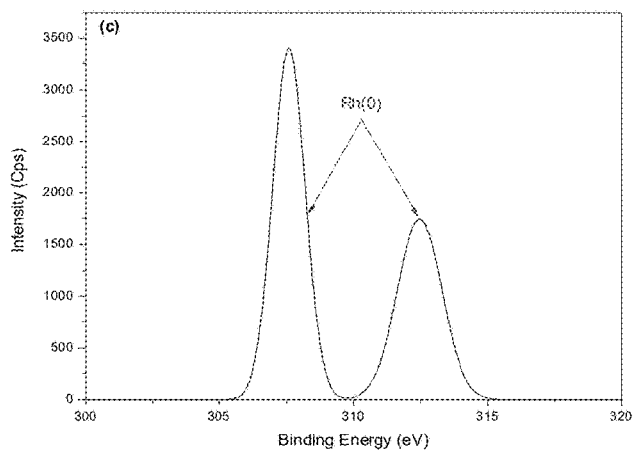
FIG. 1C illustrates a graph showing exposure to $H_2$ alone resulting in a catalyst with very low activity initially due to the formation of zerovalent Rh species as confirmed by XPS.

After pre-treating the sample of La—Rh/activated carbon catalyst with a flow of Helium at 240° C. for 2 h, four XPS peaks are observed in the region of 300 to 330 eV indicative of $Rh^{+3}$ and $Rh^0$ oxidation states, respectively (FIG. 1a). Treatment of Rh—La/activated carbon catalyst with CO alone or CO with a low concentration of $H_2$ at 240° C. (the preferred activation condition) provides a spectrum that suggests the presence of $Rh^{+1}$ and $Rh^{+3}$ (FIG. 1b). Exposure to $H_2$ alone (a procedure typically used to activate precious metals) can result in a catalyst with very low activity initially due to the formation of zerovalent Rh species as confirmed by XPS (FIG. 1c).

The carbon monoxide may be introduced at a pressure in the range of 1 to 40 atm (600 psi) but preferably in the range of 1 to 3 atm (50 psi). The fixed bed reactor where the catalyst is placed may be preheated to the desired temperature, such as, for example in the range of 170 to 360° C., but preferably in the range of 200 to 280° C.

In one embodiment, the Rh active form in the gas phase methanol carbonylation has an initial oxidation state of +1 or +3, preferably +1 after the catalyst activation.

In another embodiment, the catalyst is activated with a CO rich stream or synthesis gas (mix of $H_2$ and CO) with a CO to $H_2$ molar ratio higher than 1, preferably between 2 to 10, more preferably between 4 to 10.

EXAMPLE I

Preparation of 0.6% Rh-0.4% La Catalyst 100 g of activated carbon (granule form) is pretreated with 300 mL of $HNO_3$ (4M) at 80° C. for 6 h, then washed with distillate (or demineralized) water until pH=6.5 and outgassed under vacuum at 100° C. overnight.

Rhodium and lanthanum precursor solution mixture is first prepared by dissolving 1.22 g of rhodium trichloride and 0.50 g of lanthanum oxide in 50 mL of 37% HCl and 100 mL of distilled (or demineralized) water solution and then subjected to magnetic stirring under heating using an oil bath. The pretreated activated carbon is added to the precursor solution and dried at 60-80° C. with frequent shaking until free-flowing. The resulting catalyst is then fully dried at 120° C. overnight and subsequently activated at 400° C. for 4 h under a nitrogen flow of 1 L/min.

Alternatively, the activated carbon is pretreated after the Rh—La impregnation step. Further, the activated carbon pre-treatment is not required for the co-impregnation step.

EXAMPLE II

Methanol Carbonylation

According to the operating conditions mentioned in U.S. Pat. No. 8,436,215 or 8,088,832, the catalyst prepared as in Example I is tested in a fixed bed reactor. The mixture of renewable methanol and carbon monoxide (CO) reacted in the presence of the catalysts described herein to produce a mixture comprising methyl acetate, acetic acid, water, unreacted methanol, and dimethyl ether (DME). Methyl acetate and acetic acid are found to be produced with a molar selectivity of about 88% and 4.3%, respectively.

Table 2 shows that the average size of the Rh once activated before or after the reaction does not change significantly. Therefore, there is no sintering of Rh on the catalyst after the reaction.

EXAMPLE III

Preparation of 0.2% Rh-0.2% La Catalyst

The procedure of Example I is repeated, except that 0.41 g of rhodium trichloride and 0.23 g of lanthanum oxide dissolved in 50 mL of 37% HCl and 100 mL of distilled (or demineralized) water solution are mixed with 100 g of pretreated activated carbon. At the end of drying overnight Rh—La catalyst is recovered and subsequently activated at 400° C. for 4 h under a nitrogen flow of 1 L/min.

EXAMPLE IV

Methanol Carbonylation

When methanol carbonylation procedure of Example II is repeated but employing catalyst prepared as in Example III, methyl acetate and acetic acid molar selectivity are about 82% and 1.2%, respectively. Rh-containing catalysts prepared as in Examples I and III show a similar selectivity to methyl acetate superior to 80%. From previous results, it can be concluded that catalyst prepared as in Example I containing a higher Rh content of 0.6% show to be less sensitive to leach compared to catalyst prepared as in Example III with 0.2% of Rh.

EXAMPLE V

Comparison with a Commercial Formulation

To illustrate the differences between the performance of the catalyst prepared as in Example I and a commercial Rh based catalyst, these are tested in the methanol carbonylation reaction following the procedure of Example II. The most significant difference is observed mainly in the molar selectivity towards methyl acetate (71.4%) by using the commercial Rh based catalyst, more than 15% less compared to catalyst prepared in Example I, which gives 88%. On the other hand, acetic acid selectivity is 7.4% by using the commercial Rh-based catalyst, a slightly higher of almost 3% selectivity than catalyst prepared in Example I (4.3%).

The above results show that methanol carbonylation reaction by using the catalyst prepared as in Example I give a better compromise between results compared to commercial Rh based catalyst. The fact that catalyst prepared as in Example I is less selective to acetic acid facilitates the final products separation, reduces the corrosion risks and, with it, simplifies the process operation.

While the present disclosure has been described in connection with specific embodiments thereof, it will be understood that it is capable of further modifications and this application is intended to cover any variations, uses, or adaptations, including such departures from the present disclosure as come within known or customary practice within the art and as may be applied to the essential features hereinbefore set forth, and as follows in the scope of the appended claims.

What is claimed is:

1. A process for carbonylation of methanol comprising the step of reacting in a gas phase in a carbonylation reactor the methanol, carbon monoxide in the presence of a catalyst, producing a mixture of methyl acetate, acetic acid, water, unreacted methanol and dimethyl ether (DME), wherein said catalyst comprises at least one element from group VIII of the periodic table, an anchor consisting of one element from group III of the periodic table; and an inert support, wherein the anchor and the at least one element from group VIII of the periodic table forming an alloy and the anchor binds the one element from group VIII of the periodic table to the inert support.

2. The process of claim 1, wherein the at least one element from group VIII and Ill are in an oxide form.

3. The process of claim 1, wherein the at least one element from group VIII is iron, ruthenium, osmium, hassium, cobalt, rhodium (Rh), iridium, nickel, palladium, or platinum.

4. The process of claim 1, wherein the one element from group III of the periodic table is lanthanide (La).

5. The process of claim 1, said catalyst comprising rhodium (Rh) and lanthanide (La) alloy.

6. The process of claim 5, wherein said catalyst comprising a Rh—La alloy dispersion of greater than 80%.

7. The process of claim 5, wherein the catalyst comprises 0.6 wt % Rh-0.4 wt % La or 0.2 wt % Rh-0.2 wt % La.

8. The process of claim 1, wherein the at least one element from group VIII is cobalt, rhodium, iridium, nickel, and a mixture thereof.

9. The process of claim 1, wherein the catalyst comprises between 0.01 wt % to 1 wt % of the at least one element from group VIII compared to the total weight of the catalyst.

10. The process of claim 1, further comprising at least one transition metal.

11. The process of claim 1, further comprising at least one promotor from group III of the periodic table.

12. The process of claim 1, wherein the promotor is scandium, yttrium, lanthanum, an actinide or a mixture thereof.

13. The process of claim 1, wherein the catalyst comprises between 0.01 wt % to 1 wt % of the promotor from Group III compared to the total weight of the catalyst.

14. The process of claim 1, wherein the support is an activated carbon, a zeolite, alumina, or a mixture thereof.

15. The process of claim 1, wherein the support is chemically pretreated increasing the support surface oxygen groups.

16. The process of claim 15, wherein the support is chemically pretreated with an acid treatment.

17. The process of claim 1, wherein the carbonylation reactor is a fixed bed reactor.

18. The process of claim 1, wherein the catalyst is activated with carbon monoxide, a synthesis gas, or a mixture thereof, prior to the reacting step.

19. The process of claim 1, wherein the molar selectivity of producing methyl acetate is of at least 80%.

20. The process of claim 1, wherein the methanol is from Municipal Solid Waste (MSW), biomass, or algae.

* * * * *